United States Patent
Locke et al.

(10) Patent No.: US 10,293,088 B2
(45) Date of Patent: *May 21, 2019

(54) REDUCED-PRESSURE SYSTEMS AND METHODS EMPLOYING AN ULTRAVIOLET LIGHT SOURCE FOR REDUCING BIOBURDEN

(71) Applicant: KCI Licensing, Inc., San Antonio, TX (US)

(72) Inventors: Christopher Brian Locke, Bournemouth (GB); Timothy Mark Robinson, Basingstoke (GB)

(73) Assignee: KCI Licensing, Inc., San Antonio, TX (US)

(*) Notice: Subject to any disclaimer, the term of this patent is extended or adjusted under 35 U.S.C. 154(b) by 727 days.

This patent is subject to a terminal disclaimer.

(21) Appl. No.: 14/059,069

(22) Filed: Oct. 21, 2013

(65) Prior Publication Data

US 2014/0046282 A1 Feb. 13, 2014

Related U.S. Application Data

(63) Continuation of application No. 13/292,857, filed on Nov. 9, 2011, now Pat. No. 8,591,486.

(Continued)

(51) Int. Cl.
*A61M 1/00* (2006.01)
*A61M 1/36* (2006.01)
*A61M 5/178* (2006.01)
*A61M 5/32* (2006.01)
*A61M 5/00* (2006.01)

(52) U.S. Cl.
CPC ........ *A61M 1/0088* (2013.01); *A61M 1/0023* (2013.01); *A61M 1/0052* (2014.02);
(Continued)

(58) Field of Classification Search
CPC .......... A61M 1/36; A61M 1/00; A61M 5/178; A61M 5/00; A61M 5/32; A61M 35/00; A61F 13/00

See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

Ultraviolet disinfection | encyclopedia article by TheFreeDictionary. 2003.*

(Continued)

*Primary Examiner* — Tatyana Zalukaeva
*Assistant Examiner* — Ilya Y Treyger

(57) ABSTRACT

Systems and methods are provided for moving fluids from a patient to a canister and lowering or eliminating the bioburden of the canister. In one instance, a method for removing fluids from a patient includes using reduced pressure to remove fluids from a patient, delivering the fluids into a reduced-pressure conduit and into a fluid reservoir, exposing the fluids removed from the patient to a UV light source to kill pathogens to create disposable fluids, and disposing of the disposable fluids. Other systems, devices, and methods are presented.

20 Claims, 2 Drawing Sheets

Related U.S. Application Data

(60) Provisional application No. 61/414,664, filed on Nov. 17, 2010.

(52) U.S. Cl.
CPC ... *A61M 1/0094* (2014.02); *A61M 2205/7572* (2013.01); *Y10T 29/49826* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Guiles, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,423,750 A * | 6/1995 | Spiller | A61M 5/14 604/173 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,747,764 B1 * | 6/2014 | Burchman | A61L 2/0047 210/153 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2008/0264257 A1 * | 10/2008 | Ryder, III | A61L 9/20 95/291 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection,

(56) References Cited

OTHER PUBLICATIONS edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

REDUCED-PRESSURE SYSTEMS AND METHODS EMPLOYING AN ULTRAVIOLET LIGHT SOURCE FOR REDUCING BIOBURDEN

RELATED APPLICATION

This application is a continuation of U.S. patent application Ser. No. 13/292,857, entitled "Reduced-Pressure Systems and Methods Employing An Ultraviolet Light Source for Reducing Bioburden," filed 9 Nov. 2011, which claims the benefit, under 35 USC § 119(e), of the filing of U.S. Provisional Patent Application Ser. No. 61/414,664, entitled "Reduced-Pressure Systems and Methods Employing An Ultraviolet Light Source for Reducing Bioburden," filed 17 Nov. 2010. Each of the above applications are incorporated herein by reference for all purposes.

FIELD

The present disclosure relates generally to medical treatment systems and, more particularly, but not by way of limitation, to reduced-pressure systems and methods employing an ultraviolet (UV) light source for reducing bioburden or pathogen colonization.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

Fluids removed during treatment with reduced pressure should be carefully handled. The fluids are typically collected in a fluid canister. The fluids in the canister may include bacteria that grows, and accordingly the bioburden can be significant. The fluids in the canister typically cannot be discarded as domestic waste and must be discarded as a biohazard.

SUMMARY

According to an illustrative embodiment, a system for removing fluids from a patient using reduced pressure includes a reduced-pressure source for providing reduced pressure, a liquid receptor for removing fluids from the patient under the influence of reduced pressure, a canister having a fluid reservoir fluidly coupled to the reduced-pressure source, and a reduced-pressure conduit fluidly coupled between the canister and the fluid receptor. The reduced-pressure conduit has at least a UV-transparent portion. The system further includes a UV light source positioned to expose fluids traveling through the UV-transparent portion of the reduced-pressure conduit with UV light.

According to another illustrative embodiment, a method for removing fluids from a patient includes using reduced pressure to remove fluids from a patient, delivering the fluids into a reduced-pressure conduit and into a fluid reservoir, exposing the fluids removed from the patient to a UV light source to kill pathogens, and disposing of the fluids.

According to another illustrative embodiment, a method of manufacturing a system for removing fluids from a patient using reduced pressure includes providing a reduced-pressure source, forming a canister with a fluid reservoir, providing a liquid receptor for removing fluids from the patient using reduced pressure, fluidly coupling a reduced-pressure conduit between the canister and the liquid receptor. The method further includes associating a UV light source with the canister and positioning the UV light source to expose fluids from the patient to UV light.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
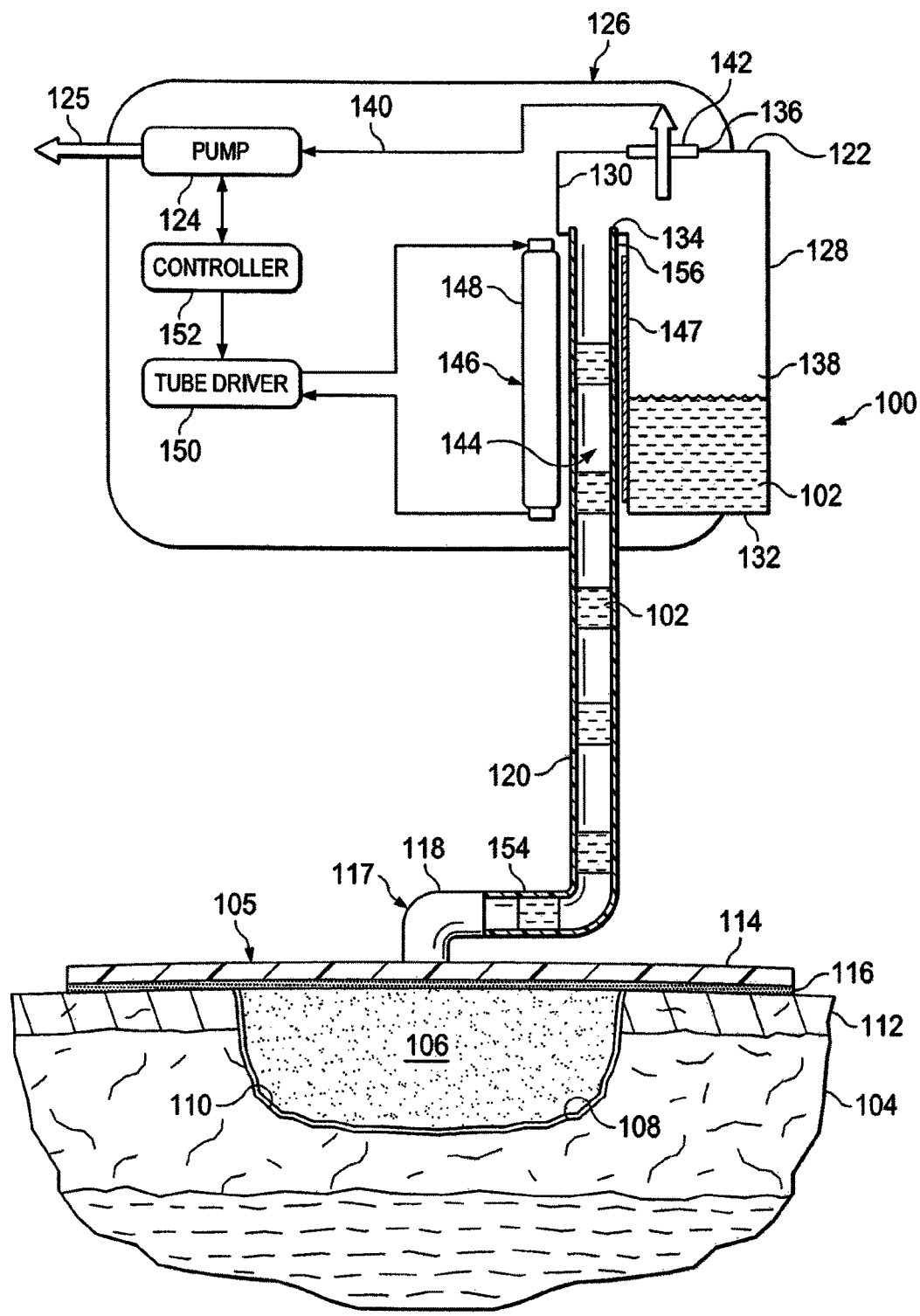
FIG. 1 is a schematic diagram, with a portion in cross section, of an illustrative embodiment of a system for removing fluids from a patient using reduced pressure and involving a UV light source.

Referring now to the drawings and initially to FIG. 1, an illustrative embodiment of a system 100 for removing fluids 102 from a patient 104 using reduced pressure is presented. The system 100 receives liquids through a liquid receptor 117, which may be, for example, a reduced-pressure dressing 105, a fluid suction subsystem, or other device or subsystem for receiving body fluids. In the illustrative embodiment, the system 100 includes the reduced-pressure dressing 105. The reduced-pressure dressing 105 is placed proximate a tissue site 108. The reduced-pressure dressing 105 may include a manifold 106, which is placed proximate the tissue site 108.

The tissue site 108 may be the bodily tissue of any human, animal, or other organism, including bone tissue, adipose tissue, muscle tissue, dermal tissue, vascular tissue, connective tissue, cartilage, tendons, ligaments, or any other tissue.

Treatment of the tissue site 108 may include removal of fluids, e.g., ascites or exudate. The tissue site 108 may be a wound, such as a wound 110 extending through epidermis 112. In another embodiment, the tissue site 108 may be an abdominal cavity, and the liquid receptor 117 may be a suction subsystem.

The term "manifold" as used herein generally refers to a substance or structure that is provided to assist in applying reduced pressure to, delivering fluids to, or removing fluids from a tissue site 108. The manifold 106 typically includes a plurality of flow channels or pathways that distribute fluids provided to and removed from the tissue site 108 around the manifold 106. In one illustrative embodiment, the flow channels or pathways are interconnected to improve distribution of fluids provided or removed from the tissue site 108. The manifold 106 comprises one or more of the following: a biocompatible material that is capable of being placed in contact with the tissue site 108 and distributing reduced pressure to the tissue site 108; devices that have structural elements arranged to form flow channels, such as, cellular foam, open-cell foam, porous tissue collections, liquids, gels, and foams that include, or cure to include, flow channels; porous materials (e.g., foam, gauze, felted mat); bioresorbable material; scaffold material; or any other material suited to a particular biological application. In one embodiment, the manifold 106 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the manifold 106 may also be used to distribute fluids such as medications, antibacterials, growth factors, and various solutions to the tissue site 108. Other layers may be included in or on the manifold 106, such as absorptive materials, wicking materials, hydrophobic materials, and hydrophilic materials.

In one illustrative embodiment, the manifold 106 may be constructed from bioresorbable materials that do not have to be removed from a patient's body following use. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 106 may further serve as a scaffold for new cell-growth, or a scaffold material may be used in conjunction with the manifold 106 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The manifold 106 is covered with a sealing member 114 to provide a sealed space for the manifold 106. The sealing member 114 may be any material that provides a fluid seal. A fluid seal is a seal adequate to maintain reduced pressure at a desired site given the particular reduced-pressure source involved. The sealing member 114 may be attached to an intact portion of the patient's epidermis 112 using an attachment device 116. The attachment device 116 may be used to secure the sealing member 114 against the patient's epidermis 112 or another layer, such as a gasket or additional sealing member. The attachment device 116 may take numerous forms. For example, the attachment device 116 may be a medically acceptable, pressure-sensitive adhesive that extends about a periphery of the sealing member 114.

The sealing member 114 may, for example, be an impermeable or semi-permeable, elastomeric material. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

A reduced-pressure interface 118 may be coupled to the sealing member 114 to provide fluid communication to the sealed space created under the sealing member 114 and in which the manifold 106 is positioned. The reduced-pressure interface 118 is fluidly coupled to a reduced-pressure conduit 120 that transports the fluids 102 to a canister 122. A reduced-pressure source 124, such as a vacuum pump, provides reduced pressure to the reduced-pressure conduit 120. The reduced pressure is delivered by the reduced-pressure interface 118 to the manifold 106 and ultimately to the tissue site 108. In one illustrative embodiment, the reduced-pressure interface 118 is a T.R.A.C.® Pad or Sensa T.R.A.C.® Pad available from KCI of San Antonio, Tex. The reduced-pressure interface 118 may be any device or arrangement allowing the reduced pressure to be delivered to the manifold 106.

The reduced-pressure source 124 provides reduced pressure. The reduced-pressure source 124 may be any device for supplying a reduced pressure, such as a vacuum pump, wall suction, micro-pump, or other source. While the amount and nature of reduced pressure applied to a tissue site 108 will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −13.5, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure. Exhaust 125 from the reduced-pressure source 124 exits the canister housing 126.

Reduced pressure is typically a pressure less than the ambient pressure at a tissue site that is being subjected to treatment. In most cases, this reduced pressure will be less than the atmospheric pressure at which the patient 104 is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure source 124 may be within a portion of the canister 122 or may be separate. It should be noted that the embodiment of FIG. 1 for removing fluids from the tissue site 108 is illustrative only. Other liquid receptors 117 or fluid removal devices or techniques that use reduced pressure may be used, and tissue sites other than open wounds may be treated. For example, fluids may be removed from an open abdominal cavity or may be from an ostomy bag or other source. Because fluids may be collected using other devices and techniques, the more general term "liquid receptor" 117 has been used. The liquid receptor 117 may be any device or subsystem for removing fluids 102 from a patient 104.

The canister 122 may be positioned within or be defined at least in part by the canister housing 126. The canister 122 has a plurality of walls 128, 130, 132 that form a fluid reservoir 138 for receiving and retaining the fluids 102 from the patient 104. The walls 128, 130, 132 may be orthogonal, tapered, curved, or other shapes. The canister 122 may include a first port 134 and a second port 136. In the illustrative embodiment shown, the reduced-pressure conduit 120 is fluidly coupled to the first port 134 for delivering the fluids 102 into the fluid reservoir 138. A reduced-pressure supply conduit 140 may fluidly couple the reduced-pressure source 124 and the second port 136. The reduced-pressure source 124 thereby provides reduced pressure into the fluid reservoir 138. A hydrophobic filter 142 may be associated with the second port 136 to prevent fluids 102, particularly liquids, from entering a reduced-pressure supply conduit 140 and arriving at the reduced-pressure source 124.

A UV-transparent portion 144 of the reduced-pressure conduit 120 is transparent to UV light. A UV light source 146 is positioned proximate to the UV-transparent portion 144 to expose at least the UV-transparent portion 144 of the reduced-pressure conduit 120 to UV light. For example, the UV transparent portion 144 may be positioned within the canister housing 126 and the UV light source 146 may be positioned in the canister housing 126 to expose the UV-transparent portion 144 to UV light. Thus, the UV light waves from the UV light source 146 enter the reduced-pressure conduit 120 through the UV-transparent portion 144 and expose the fluids therein as the fluids pass through the reduced-pressure conduit 120. It should be apparent that the UV light source 146 may be associated with the reduced-pressure canister 122 or reduced-pressure conduit 120 in many ways, such as by securing the UV light source 146 to a portion of the canister housing 126 or by securing the UV light source 146 to the reduced-pressure conduit 120.

The UV light source 146 may include a tube driver 150 and at least one UV light tube 148. The UV light source 146 may be positioned proximate the UV-transparent portion 144. The UV light source 146 may be coupled to the canister 122 such that fluids 102 are exposed to UV light when traveling through the UV-transparent portion 144 of the reduced-pressure conduit 120. The UV light source 146 may include one or more reflectors 147 to focus or redirect at least a portion of the UV light. The UV light source 146 may utilize bands A, B, or C to kill pathogens. In one instance, the UV light source 146 may be a Dymax Blue Wave 50 machine by Dymax Corporation of Torrington, Conn. Unless otherwise indicated, as used throughout this document, "or" does not require mutual exclusivity. Any suitable UV light source may be used. In this embodiment, the UV light tube 148 may be positioned at various distances from the fluids to be exposed. For example, the UV light tube 148 may be as close as the thickness of a plastic or glass wall, e.g., about 0.5 mm, or may be spaced at a distance equal to the width of the canister 122 or greater. The UV light tube 148 will typically be between about 0.5 mm and about 10 mm from the fluids or a portion of the fluids.

The one or more UV light tubes 148 may be electrically coupled to the tube driver 150. The tube driver 150 provides energizing power to the one or more UV light tubes 148. A controller 152 may be coupled to the reduced-pressure source 124 or the tube driver 150 to provide control. The controller 152 may be a printed wire assembly (PWA) or an application specific integrated circuit (ASIC) or other control device.

In operation, according to one illustrative embodiment, the liquid receptor 117 receives fluids from the patient 104 and facilitates delivery of the fluids to the reduced-pressure conduit 120. For example, the reduced-pressure dressing 105, which serves as a liquid receptor 117, is placed proximate the tissue site 108, and a first end 154 of the reduced-pressure conduit 120 is fluidly coupled to the reduced-pressure interface 118. A second end 156 of the reduced-pressure conduit 120 is fluidly coupled to the fluid reservoir 138 with the UV-transparent portion 144 proximate to the UV light source 146. The system 100 is activated such that the reduced-pressure source 124 delivers reduced pressure to the fluid reservoir 138. Because of the fluid couplings, the reduced pressure is delivered to the tissue site 108. The fluids 102 are removed and delivered to the fluid reservoir 138.

When the UV light source 146 is activated, the fluids 102 passing at least through the UV-transparent portion 144 of the reduced-pressure conduit 120 are exposed to UV light from the UV light source 146. The exposure to UV light may be continuous or may be pulsed. For example, the UV light source 146 may be pulsed, e.g., 1-60 seconds, 2 minutes, or some other duration to kill a desired level of pathogens. The UV light source 146 may include numerous power options and wavelengths. For example, a C-band (approximately 254 nm) at a power of 100-300 microwatts per $cm^2$ may be used, but numerous other settings are possible. The exposure of the fluids 102 to the UV light from UV light source 146 kills a majority of pathogens in the fluids 102. For example, 90%, 95%, 98%, 99% or more pathogens in the fluids 102 may be killed.

For fluids initially containing pathogens, as the majority of pathogens in the fluids 102 are killed, disposable fluids are formed. The disposable fluids may not require handling as a biohazard or hazardous waste, but may be treated as domestic waste. As used herein, "disposable fluids" are fluids from which living pathogens are substantially absent or at acceptable levels. The disposable fluids formed by killing a majority of the pathogens in the fluids present a relatively decreased bioburden. In instances in which a majority of the pathogens in the fluids have been killed, reflux or spills of the fluids present relatively less risk than the reflux or spills otherwise would. In some embodiments, after removing the fluids 102 from a patient 104 using the system 100, the fluid reservoir 138 is disengaged from the canister housing 126. The fluid reservoir 138, which contains disposable fluids, may be discarded as non-hazardous waste or domestic waste. The remaining portions of the canister housing 126 may be reconditioned, e.g., sterilized, and reused with a new fluid reservoir 138.

It should be noted that while the reduced-pressure conduit 120 is shown in FIG. 1 running parallel to UV light tube 148, other arrangements are contemplated. For example, the reduced-pressure conduit 120 may be wrapped around the UV light source 146, e.g., around the UV light tube 148, in a swirling fashion to provide additional exposure to UV light. In another embodiment, the UV light tube 148 of the UV light source 146 may be wrapped around the UV-transparent portion 144 of the reduced-pressure conduit 120. It should also be understood that while a single UV light tube 148 is shown, multiple UV light tubes may be used.

Figure 3:
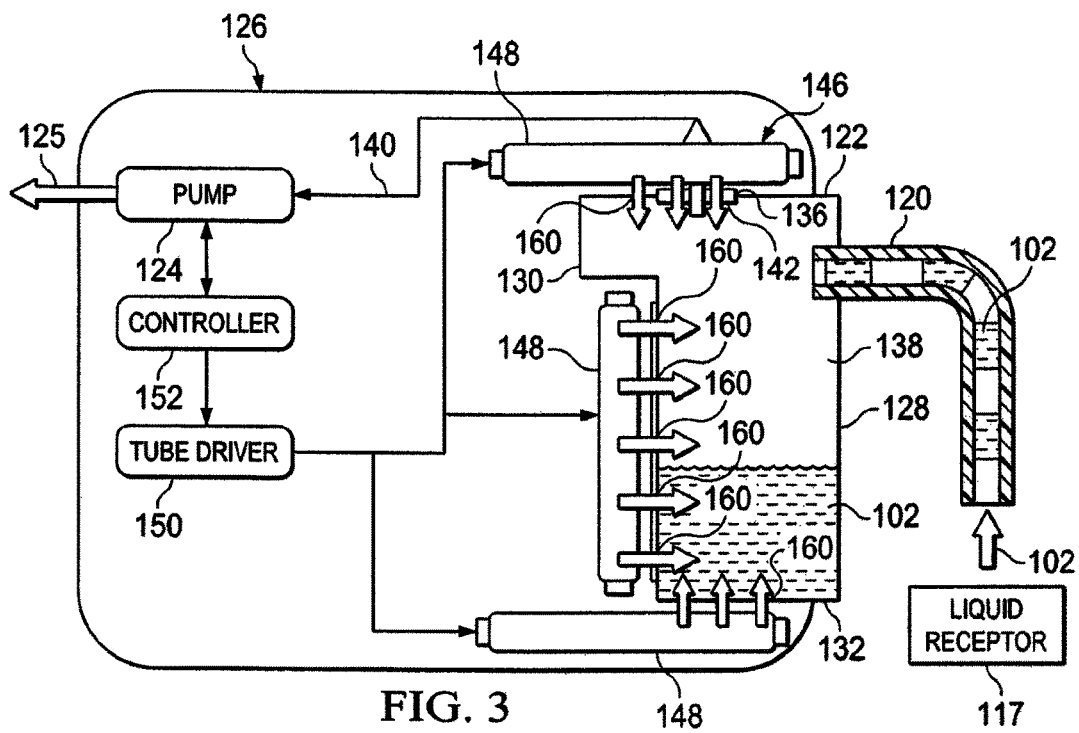
FIG. 3 is a schematic diagram of another illustrative embodiment of a portion of a system for removing fluids from a patient using reduced pressure and involving a UV light source.

Moreover, as shown in FIG. 3, multiple tubes may be placed around the canister 122 as will be described.

In preparing the canister 122 for use in the system 100, the canister 122 may be sterilized by irradiating the canister 122 with gamma radiation. The gamma radiation often causes the canister 122 to become relatively darker in tone, e.g., from a white to a dark yellow in some instances. Thus, at the time treatment using the system 100 is initiated, the canister 122 may have a darker tone relative to the pre-sterilized tone. Exposing the canister 122 to UV light may, however, modify the tone of the canister 122 to a lighter tone relative to the post-sterilization tone. In some instances, the tone of the canister 122 lightens such that the tone is substantially comparable to the original tone, i.e., the pre-sterilization tone. The change in tone may be useful in confirming effectiveness of the system 100. By noting a change in tone of the canister 122 from a relatively darker tone to a relatively lighter tone, the user may be assured that the UV light source 146 is functioning and is fully irradiating the canister 122.

Figure 2:
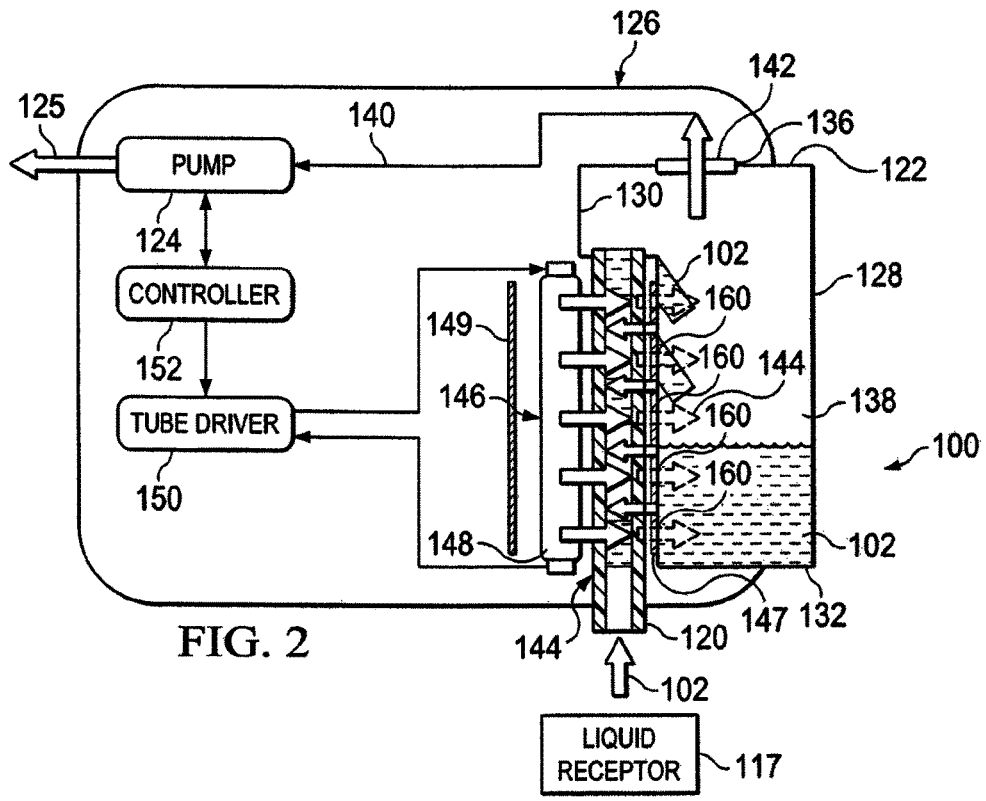
FIG. 2 is a schematic diagram of an illustrative embodiment of a portion of a system for removing fluids from a patient using reduced pressure and involving a UV light source.

Referring now primarily to FIG. 2, another illustrative embodiment of a system 100 for removing fluids 102 from a patient is presented. The system 100 is analogous in most respects to FIG. 1, and accordingly, some parts are labeled but not further described here. As in previous embodiments, the fluids 102 are removed from the patient 104 using a liquid receptor 117 and delivered through a reduced-pressure conduit 120 to a canister 122 formed with a plurality of walls, e.g., walls 128, 130, 132. In this illustrative embodiment, a portion of the wall 130 includes UV-transparent portions 160 that allow UV light from a UV light source 146 to enter into the inside of the canister 122 to kill pathogens. The UV transparent portions 160 may be used in addition to or in lieu of the UV-transparent portion 144 of the reduced-pressure conduit 120. Thus, when included as an addition, UV light entering the UV transparent portions 160 may kill any pathogens that may not have been killed as the pathogens traveled through the reduced-pressure conduit 120 in the UV-transparent portion 144. An additional reflector 149 may be added to direct UV light.

Referring now primarily to FIG. 3, another illustrative embodiment of a system 100 for removing fluids 102 is presented that is analogous to the previous illustrative embodiments with two main exceptions. First, the reduced-pressure conduit 120 may directly enter the canister 122 without exposure to a UV light source 146. Alternatively, the reduced-pressure conduit 120 may be exposed to a UV light before entering the canister 122. Second, the UV light source 146 comprises a plurality of UV light tubes 148 distributed at numerous locations relative to the canister 122. The walls 130 and 132 have UV-transparent portions 160 that allow the UV light from UV light source 146 to enter into the fluid reservoir 138. The UV light tubes 148 are configured to expose fluids within the canister 122 to UV light at least through the UV-transparent portions 160. The UV light kills substantially all the pathogens within the fluid 102 in the fluid reservoir 138. In this illustrative embodiment, the UV light source 146 may be continuously powered during operation or may be pulsed or used at intervals.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, the UV-transparent portion 144 on reduced-pressure conduit 120 shown in FIG. 1 may be incorporated with the UV light source 146 entering the canister 122 fort the arrangement shown in FIG. 3.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for removing fluids from a patient using reduced pressure, the system comprising:
   a reduced-pressure source for providing the reduced pressure;
   a liquid receptor for removing the fluids from the patient under the influence of the reduced pressure;
   a canister having a fluid reservoir configured to be fluidly coupled to the reduced-pressure source and to the liquid receptor, the canister at least partially being positioned within a canister housing and including at least one wall;
   a reduced-pressure conduit configured to fluidly couple the canister and the liquid receptor, wherein the reduced-pressure conduit includes a UV-transparent portion positioned within the canister housing; and
   a UV light source positioned in the canister housing to expose the fluids to UV light through the UV-transparent portion of the reduced-pressure conduit and a UV-transparent portion of the at least one wall of the canister.

2. The system of claim 1, wherein:
   the liquid receptor comprises a wound dressing, the wound dressing comprising:
      a manifold for providing the reduced pressure to a tissue site on the patient, and
      a sealing member covering the manifold and forming a fluid seal; and
   the at least one wall of the canister comprises a plurality of walls forming the fluid reservoir.

3. The system of claim 1, wherein the UV light source comprises a tube driver and at least one UV tube.

4. The system of claim 1, wherein:
   the at least one wall of the canister comprises a plurality of walls;

wherein the plurality of walls comprise a plurality of UV-transparent portions; and
the UV light source comprises a plurality of UV lights positioned proximate the plurality of UV-transparent portions.

5. The system of claim 1, wherein the UV light source is configured to kill at least 95% of pathogens in the fluids.

6. The system of claim 1, wherein the UV light source is coupled to the canister.

7. A system for removing fluids from a patient using reduced pressure, the system comprising:
a reduced-pressure source for providing the reduced pressure;
a liquid receptor for removing the fluids from the patient under the influence of the reduced pressure;
a canister having a fluid reservoir configured to be fluidly coupled to the reduced-pressure source and to the liquid receptor, the canister at least partially being positioned within a canister housing, the fluid reservoir comprising a wall;
a reduced-pressure conduit including a UV-transparent portion configured to be fluidly coupled between the canister and the liquid receptor; and
a UV light source positioned in the canister housing to expose the fluids to UV light through a UV-transparent portion of the wall of the fluid reservoir and the UV-transparent portion of the reduced-pressure conduit.

8. The system of claim 7, wherein:
the liquid receptor comprises a wound dressing, the wound dressing comprising:
a manifold for providing reduced pressure to a tissue site on the patient; and
a sealing member covering the manifold and forming a fluid seal.

9. The system of claim 7, wherein the UV light source comprises a tube driver and at least one UV tube.

10. The system of claim 7, wherein:
the wall of the fluid reservoir comprises a plurality of walls;
the plurality of walls comprise a plurality of UV-transparent portions; and
the UV light source comprises a plurality of UV lights positioned proximate the plurality of UV-transparent portions.

11. The system of claim 7, wherein the UV light source is configured to kill at least 95% of pathogens in the fluids.

12. The system of claim 7, wherein the UV light source is coupled to the canister.

13. The system of claim 7, the wall of the fluid reservoir comprising a plurality of UV-transparent portions, the UV-light source being positioned proximate the plurality of UV-transparent portions.

14. The system of claim 7, the wall of the fluid reservoir comprising a plurality of UV-transparent portions, the UV-light source comprising a plurality of UV lights positioned proximate the plurality of UV-transparent portions.

15. The system of claim 1, wherein at least a portion of the reduced-pressure conduit is positioned between the UV light source and the fluid reservoir.

16. The system of claim 1, wherein the UV light source is configured to expose the fluids to pulsed UV-light.

17. The system of claim 1, wherein the UV light source is configured to expose the fluids to continuous UV-light.

18. The system of claim 7, wherein at least a portion of the reduced-pressure conduit is positioned between the UV light source and the fluid reservoir.

19. The system of claim 7, wherein the UV light source is configured to expose the fluids to pulsed UV-light.

20. The system of claim 7, wherein the UV light source is configured to expose the fluids to continuous UV-light.

* * * * *